United States Patent
Li et al.

(10) Patent No.: US 6,630,443 B2
(45) Date of Patent: *Oct. 7, 2003

(54) HUMAN AMINE TRANSPORTER ANTIBODIES

(75) Inventors: Yi Li, Gaithersburg, MD (US); Liang Cao, Hong Kong (CN); Craig A. Rosen, Laytonsville, MD (US)

(73) Assignee: Human Genome Sciences, Inc., Rockville, MD (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/502,018

(22) Filed: Feb. 11, 2000

(65) Prior Publication Data

US 2003/0157103 A1 Aug. 21, 2003

Related U.S. Application Data

(60) Division of application No. 09/139,675, filed on Aug. 25, 1998, now Pat. No. 6,117,426, which is a division of application No. 08/471,496, filed on Jun. 6, 1995, now Pat. No. 5,798,223, which is a continuation-in-part of application No. PCT/US95/02645, filed on Mar. 1, 1995.

(51) Int. Cl.⁷ .......................... C07K 16/18; C12P 21/00
(52) U.S. Cl. .......................... 514/2; 435/7.1; 435/70.1; 530/350; 530/387.9
(58) Field of Search .............................. 530/387.9, 350, 530/387.3, 388.1, 388.22, 389.1; 424/134.1, 133.3, 139.1; 514/2; 435/7.1, 70.1

(56) References Cited

U.S. PATENT DOCUMENTS

| | | | |
|---|---|---|---|
| 5,688,936 A | 11/1997 | Edwards | ..................... 536/23.5 |
| 5,859,200 A | 1/1999 | Li et al. | ..................... 530/350 |

FOREIGN PATENT DOCUMENTS

| | | |
|---|---|---|
| WO | WO 93/25699 | 12/1993 |
| WO | WO 94/16718 | 8/1994 |

OTHER PUBLICATIONS

Erickson, J.D., and Eiden, L.E., "Functional Identification and Molecular Cloning of a Human Brain Vesicle Monoamine Transporter," *J. Neurochem.* 61:2314–2317 (1993).

Weihe, E., et al., "Localization of Vesicular Monoamine Transporter Isoforms (VMAT1 and VMAT2) to Endocrine Cells and Neurons in Rat," *J. Mol. Neuro.* 5:149–164 (1994).

Erickson, J.D. et al., Functional identification and molecular cloning of a human brain vesicle monoamine transporter. J. Neurochemistry 61(6):2314–2317 (1993).

Weihe, E. et al., Localization of vesicular monoamine transporter isoforms (VMAT1 and VMAT2) to endocrine cells and neurons in rat. J. Molecular Neuroscience 5(3):149–164 (1994).

Supplementary Partial European Search Report from EP 95916097.9.

Erickson, J.D. et al. "Expression cloning of a reserpine–sensitive vesicular monoamine transporter," *Proc. Natl. Acad. Sci. USA* 89:10993–10997 (1992).

Erickson, J.D. et al., "Distinct pharmacological properties and distribution in neurons and endocrine cells of two isoforms of the human vesicular monoamine transporter," *Proc. Natl. Acad. Sci. USA* 93:5166–5171 (May 1996).

Krejci, E. et al., "Expression and regulation of the bovine vesicular monoamine transporter gene," *FEBS Lett.* 335:27–32 (1993).

Lerner, R.A., "Tapping the immunological repertoire to produce antibodies of predetermined specificity," *Nature* 299:592–596 (1982).

Liu, Y. et al., "A cDNA That Supresses MPP⁺ Toxicity Encodes a Vesicular Amine Transporter," *Cell* 70:539–551 (1992).

Liu, L. et al., "The molecular cloning and expression of a human synaptic vesicle amine transporter that suppresses MPP⁺ toxicity," *Brain Res. Mol. Brain Res.* 25:90–96 (1994).

Peter, D. et al., "Chromosomal Localization of the Human Vesicular Amine Transporter Genes," *Genomics* 18:720–723 (1993).

Sambrook, J. et al., Eds., *Molecular Cloning: A Laboratory Manual*, 2nd ed., Cold Spring Harbor Laboratory Press: Cold Spring Harbor, NY, pp. 9.50–9.51, 11.3–11.15 (1989).

Surratt, C.K. et al., "A human synaptic vesicle monoamine transporter cDNA predicts posttranslational modifications, reveals chromosome 10 gene localization and identifies TaqIRFLPS," *FEBS Lett.* 318:325–330 (1993).

Wall, S.C. et al., "Biogenic amine flux mediated by cloned transporters stably expressed in cultured cell lines: amphetamine specificity for inhibition and efflux," *Mol. Pharmacol.* 47:544–550 (1995).

GenBank Accession No. x71354, from Lesch, K.P. et al., "*H. sapiens* mRNA for vesicular monoamine transporter," (1993) (No alignment).

GeneSeq Accession No. R47342, from Edwards, R.H., "Mammalian synaptic vesicle amine transporter protein," (1993) (No alignment).

GenBank Accession No. D28289, Minobe, Y. and Sasaki, T., "RICR0716A Rice root Oryza sativa cDNA, mRNA sequence," (Dec. 1994) (No alignment).

*Primary Examiner*—Lorraine Spector
(74) *Attorney, Agent, or Firm*—Human Genome Sciences, Inc.

(57) ABSTRACT

A Human amine transporter polypeptide and DNA (RNA) encoding such polypeptide and a procedure for producing such polypeptide by recombinant techniques is disclosed. Also provided are methods for detecting agonists and antagonists to such polypeptide and the use of agonists and antagonists for treating diseases related to the underexpression and over-expression of the Human amine transporter of the present invention. Also disclosed are methods for detecting mutations in the nucleic acid sequence encoding the polypeptide and for detecting altered levels of the soluble form of the polypeptide.

12 Claims, 7 Drawing Sheets

TCCTGCGTTATCCCCCTGATTCTGTGGATAACCGTATTNCGCCTTTGAGTGAGCTGATA
CCGCTCNCNCAGCCGAACGACCGAGCGCAGCGAGTCAGTGAGCGAGGAAGCGGAAGAGC
GCCAATACGCAAACCGCCTCTCCCCGCGTTGGCCGATTCATTAATGCAGCTGGCACG
ACAGGGTTTCCCGACTGGAAAGCGGGCAGTGAGCGCAACGCAATTAATGTGAGTTAGCTCA
CTCATTAGGCACCCCAGGCTTTACACTTTATGCTTCCGGCTCGTATGTTGTGTGGAATTG
TGAGCGGATAACAATTTCACACAGGAAACAGCTATGACCATGATTACGCCAAGCTCGAAA
TTAACCCTCACTAAAGGGAACAAAAGCTGGAGCTCCACGCGGTGGCGNCCGCTCTAGAA
CTAGTGGATCCCCCGGNCTGCAGGGGCACACACATCCAACAGCACACGTTCAGAGAACACAGTGTCCCTGCTGTCT
AACAGGAGGCAATAAATCCAACATACCTCACTGAGTGCCTCACACCAACATGGGCTCCAAGTGAGTT
TGCTAACAGCTGCCAATACCTCCCTCTTCCATAAAGGCTGCAGGAGACCTGTAGCTG
TCATTCGTCTGGGCAGACTCCCTCCCCTCTTCCATAAAGGCTGCCCCAGTCCGGCCATCACCAT
TCACAGAGACCTTCCCTAAGAGCCCAGGGGGAAGACTGCCCCAGTCCGGCCATCACCAT
                                                              M
GCTCCGGCCCATTCTGGATGCTCCCAGCGGTTGCTGAAGGAGGGGAGAGGTCCCGGCA
L  R  P  I  L  D  A  P  Q  R  L  L  K  E  G  R  A  S  R  Q

FIG.1A

```
GCTGGTGCTGGTGGTGGTATTCGTCGCCTTTGCTCCTGGACAACATGCTGTTTACTGTGGT
 L  V  L  V  V  V  F  V  A  L  L  L  D  N  M  L  F  T  V  V
850                         870                         890
GGTGCCAATTGTGCCCACCTTCCTATATGACATGGAGTTCAAAGAAGTCATCTCTTCTCT
 V  P  I  V  P  T  F  L  Y  D  M  E  F  K  E  V  I  S  S  L
910                         930                         950
GCACCTCGGGCATGCCGGAAGTTCCCCACATGCCCCTCGCCTCTCCTGCCTTTTCCACCAT
 H  L  G  H  A  G  S  S  P  H  A  L  A  S  P  A  F  S  T  L
970                         990                         1010
CTTCTCCTTCTTCAACAACAACACCGTGGCTGTTGAAGAAGGCGTACCTAGTGGAATAGC
 F  S  F  F  N  N  N  T  V  A  V  E  E  S  V  P  S  G  I  A
1030                        1050                        1070
ATGGATGAATGACACTGCCAGCACCATCCCACCTCCAGCCACTGAAGCCATCTCAGCTCA
 W  M  N  D  T  A  S  T  I  P  P  P  A  T  E  A  I  S  A  H
1090                        1110                        1130
TAAAACAACTGCTTGCAAGGCACAGGTTTCTTGGAGGAAGAGACTACCCGGGTCGGGGT
 K  N  N  C  L  Q  G  T  G  F  L  E  E  E  T  T  R  V  G  V
1150                        1170                        1190
TCTGTTTGCTTCAAAGGCTGTGATGCAACTTCGTCAACCATTCGTGGGCCCTCTCAC
 L  F  A  S  K  A  V  M  Q  L  L  V  N  P  F  V  G  P  L  T
1210                        1230                        1250
CAACAGGATTGGATATCATATCCCATGTTTGCTGGCTTTGTTATCATGTTTCTCTCCAC
 N  R  I  G  Y  H  I  P  M  F  A  G  F  V  I  M  F  L  S  T
1270                        1290                        1310
AGTTATGTTTGCTTTTTCTGGGACTTACACTCTACTCTTTGTGGCCCGAACCCTTCAAGG
 V  M  F  A  F  S  G  T  Y  T  L  L  F  V  A  R  T  L  Q  G
1330                        1350                        1370
```

```
  C  V  P  L  A  H  K  N  F  G  L  I  G  P  N  A  G  L  G  L
TNCCATAGGCATGGTGGAATCTTCTATGATGCCCATCATGGGCCACCTGGTGGATCCCACG
                    1930                    1950                    1970
  X  I  G  M  V  E  S  S  M  M  P  I  M  G  H  L  V  D  P  R
CCACACCTCGGTGTATGGGAGTGTCCACGCCATGCTGGCTGTGGCTTTTTGCATGGGCTT
                    1990                    2010                    2030
  H  T  S  V  Y  G  S  V  H  A  I  A  D  V  A  F  C  M  G  F
TGCTATAGGCTATTCTGAGTCAGGACTGCCCCATGGAGACCCGGATGTATCAACCCAGAA
                    2050                    2070                    2090
  A  I  G  Y  S  E  S  G  L  P  H  G  O  P  D  V  S  T  Q  K
ACCTCTTCCCTGACCAGTCACCATGGCTGACCCACGGGCTCAGTGGCCTCAAAACCTCTG
                    2110                    2130                    2150
  P  L  P  W  T  S  H  H  G  *
CCTGGGATCTTCTTCCTCCCCTCCCATGGACACTGTCCCTGATACTCTTCTCACCTGTGT
                    2170                    2190                    2210
AACTTGTAGCTCTTCMTCTATGCCTTGGTGCCGCAGTGGCCCATCTTTTATGGGAAGACA
                    2230                    2250                    2270
GAGTGATGCACCYCCCGCTGCTGTGAGGTTGATTAAACTTGAGCTGTGACGGGGTTCTG
                    2290                    2310                    2330
CAAGGGGTGACTCATTGYATAGAGGTGGTAGTGAGTAATGTGCCCTGAAACCAGTGGGG
                    2350                    2370                    2390
TGACTGACAAGCTCTTTAATCTGTTGCCTGATTTCTCTGGCATAGCCCCAACAGATCG
                    2410                    2430                    2450
GAAGAGTGTTACCCTCTTTwCCCTCAAGTGTTCTTTCCGGGTTTCCCCAGCCGAGTT
                    2470                    2490                    2510
```

FIG. 1D

```
                                                     2570
                              2550
            2530
GAGAAAATGTTCTCAGCATTGTCTTGCTGCCAAATGCCAGCKTGAAGAGTTWGGTATGKT
                    2590                    2610                    2630
TTTTCTNCCATTTATTTTATTTATTWACTAAAGTGAATGATTTTACTGTGGYTAAATCTA
            2650                    2670                    2690
GAGCTGCTAAAAGGGCTTTACCCCTCAGTGAAAAGTGTCTTCTATTTNCATWATCTTTCAG
                    2710                    2730                    2750
AAACWGGAGCCCATTTCTCTTCTCGGTGGAGTTATNGACATCCTCCTGACCNCCCCCTGTGT
            2770                    2790                    2810
NTNCCTACCTNTACTGAACCTCTTAGACTCTNAGAAATAAAAGTAGAAGAAAGACAGAAA
                    2830                    2850                    2870
AATTAACTGATTAGACCCAAGATTTCATGGAAGAAGTTAAAAGAAAACTGCCTTGGAAAT

CCCTC
```

FIG. 1E

Homology Alignment between HATBG78 and
the Rat Amine Transporter

```
  1 MLRPILDAPQRLLKEGRASRQLVLVVVFVALLLDMMFTVVVPIVPTFLY  50
    ||..:|||||||||||||..||.||||||||||||:|||||||||||||
  1 MQVVTGAPQRLLKEGRQSRKLVLVVVFVALLLDNMLLTVVVPIVPTFLY  50

51 DMEFKEVISSLHLGHAGSSPHALASPAFSTIFSFFNNNTVAVEESVPSGI 100
    |||  ||||  ||.|| ..::||||||||||||.|:..|.||
 51 ATEFKDSNSSLHRGPSVSSQQALTSPAFSTIFSFFQNTTTVEEHVPFRV 100

101 AWMNDTASTIPPPATEAISAHKNNCLQGTGFLEEETTRVGVLFASKAVMQ 150
    |.|.:|||||| ||.|.:.|||||||||:||||||:|.|||||||:|||
101 TW...TNGTIPPPVTEASSVPKNNCLQGIEFLEEENVRIGILFASKALMQ 147

151 LLVNPFVGPLTNRIGYHIPMFAGFVIMFLSTVMFAFSGTYTLLFVARTLQ 200
    |||||||||||||||||||||||.||||||||||||||||||||||||||
148 LLVNPFVGPLTNRIGYHIPMFVGFMIMFLSTLMFAFSGTYALLFVARTLQ 197

201 GIGSSFSSVAGLGMLASVYTDDHERGRAMGTALGGLALGLLVGAPFGSVM 250
    ||||||||||||||||||||||:||||||||:||||||||||||||||||
198 GIGSSFSSVAGLGMLASVYTDNYERGRAMGIALGGLALGLLVGAPFGSVM 247
```

FIG.2A

```
251 YEFVGKSAPFLILAFLALLDGALQLCILQPSKVSPESAKGTPLFMLLKDP 300
    |||||||:|||||||||||||||||||||||||||||||||:||::||||
248 YEFVGKSSPFLILAFLALLDGALQLCILWPSKVSPESAMGTSLLTLLKDP 297

301 YILVAAGSICFANMGVAILEPTLPIWMMQTMCSPKWQLGLAFLPASVSYL 350
    |||||||||||.||||||||||||||||||||||.||||||||||||:|
298 YILVAAGSICLANMGVAILEPTLPIWMMQTMCSPEWQLGLAFLPASVAYL 347

351 IGTNLFGVLANKMGRWLCSLIGMLVVGTSLLCVPLAHKNFGLTGPNAGLG 400
    |||||||||||||||||:||:|::|.|||||||||||:|||||||||||
348 IGTNLFGVLANKMGRWLCSLVGMVAVGISLLCVPLAHNIFGLIGPNAGLG 397

401 LXIGMVESSMMPIMGHLVDPRHTSVYGSVHAIADVAFCMGFAIGYSESGL 450
    :|||||||:||||||||||:|||||||||:|||||||||:||||||::|
398 FAIGMVDSSLMPIMGYLVDLRHTSVYGSVYAIADVAFCVGFAIGPSTGGV 447

451 PHGDPDVSTQKPLPWTSH 468
    ::|:|::|::|||
448 IVQVIGFPWLMVIIGTIN 465
```

FIG.2B

HUMAN AMINE TRANSPORTER ANTIBODIES

This application is a divisional of U.S. application Ser. No. 09/139,675, filed Aug. 25, 1998, which is now U.S. Pat. No. 6,117,426, which is a divisional of U.S. application Ser. No. 08/471,496, filed Jun. 6, 1995, which is now U.S. Pat. No. 5,798,223, which is a Continuation-in-Part of PCT/US95/02645, filed Mar. 1, 1995, published as WO 96/27009 on Sep. 6, 1996 in English. The full disclosures of each of these is herein incorporated by reference.

FIELD OF THE INVENTION

This invention relates to newly identified polynucleotides, polypeptides encoded by such polynucleotides, the use of such polynucleotides and polypeptides, as well as the production of such polynucleotides and polypeptides. More particularly, the polypeptide of the present invention is a human amine transporter. The invention also relates to inhibiting the action of such polypeptides.

RELATED ART

Neurosensory and neuromotor functions are carried out by neurotransmission. Neurotransmission is the conductance of a nerve impulse from one neuron, called the presynaptic neuron, to another neuron, called the postsynaptic neuron, across the synaptic cleft. Transmission of the nerve impulse across the synaptic cleft involves the secretion of neurotransmitter substances. The neurotransmitter is packaged into vesicles in the presynaptic neuron and released into the synaptic cleft to find its receptor at the postsynaptic neuron. Transmission of the nerve impulse is normally transient.

An essential property of synaptic transmission is the rapid termination of action following neurotransmitter release. For many neurotransmitters, including catecholamine, serotonin, and certain amino acids (e.g., gamma-aminobutyric acid (GABA), glutamate and glycine), rapid termination of synaptic action is achieved by the uptake of the neurotransmitter into the presynaptic terminal and surrounding glial cells. This rapid re-accumulation of a neurotransmitter is the result of re-uptake by the presynaptic terminals.

At presynaptic terminals, the various molecular structures for re-uptake are highly specific for such neurotransmitters as choline and the biogenic amines (low molecular weight neurotransmitter substances such as dopamine, norepinephrine, epinephrine, serotonin and histamine). These molecular apparatuses are termed transporters. These transporters move neurotransmitter substances from the synaptic cleft back across the cell membrane of the presynaptic neuron into the cytoplasm of the presynaptic terminus and therefore terminate the function of these substances. Inhibition or stimulation of neurotransmitter uptake provides a means for modulating the effects of the endogenous neurotransmitters.

Re-uptake of neurotransmitter substances by the transporters may be sodium-dependent. For instance, the GABA transporter is a member of the recently described sodium-dependent neurotransmitter transporter gene family. These transporters are transmembrane receptor complexes having an extracellular portion, a transmembrane portion and an intracellular portion. A significant degree of homology exists in the transmembrane domains of the entire family of sodium-dependent neurotransmitter transporter proteins, with considerable stretches of identical amino acids, while much less homology is apparent in the intracellular and extracellular loops connecting these domains. The extracellular loop in particular seems to be unique for each transporter. This region may contribute to substrate and/or inhibitor specificities.

Identifying the novel amine transporter of the present invention and elucidating the structural and functional distinctions between different types of transporters is important in understanding the cellular and molecular bases of behavior and disease.

SUMMARY OF THE INVENTION

The polypeptide of the present invention has been putatively identified as an amine transporter. This identification has been made as a result of amino acid sequence homology to the rat amine transporter.

In accordance with one aspect of the present invention, there is provided a novel mature polypeptide which is a human amine transporter, as well as biologically active and diagnostically or therapeutically useful fragments, analogs and derivatives thereof.

In accordance with another aspect of the present invention, there are provided isolated nucleic acid molecules encoding a human amine transporter, including mRNAs, DNAs, cDNAs, genomic DNAs as well as analogs and biologically active and diagnostically or therapeutically useful fragments and derivatives thereof.

In accordance with yet a further aspect of the present invention, there is provided a process for producing such polypeptide by recombinant techniques comprising culturing recombinant prokaryotic and/or eukaryotic host cells, containing a human amine transporter nucleic acid sequence, under conditions promoting expression of said protein and subsequent recovery of said protein.

In accordance with yet a further aspect of the present invention, there is provided a process for utilizing such polypeptide, or polynucleotide encoding such polypeptide for screening for agonists and antagonists and ligands to such polypeptide.

In accordance with yet a further aspect of the present invention, there is provided a method for utilizing such agonists for stimulating the amine transporter uptake of neurotransmitter ligands for the treatment of diseases related to under-expression of the amine transporter or over-expression of the ligand.

In accordance with yet another aspect of the present invention, there is also provided a process for using antagonists for inhibiting the amine transporter uptake of neurotransmitter ligands for the treatment of diseases related to over-expression of the amine transporter or under-expression of the ligand.

In accordance with yet a further aspect of the present invention, there are provided antibodies against such polypeptides.

In accordance with yet a further aspect of the present invention, there are also provided nucleic acid probes comprising nucleic acid molecules of sufficient length to specifically hybridize to human amine transporter sequences.

In accordance with still another aspect of the present invention, there are provided diagnostic assays for detecting diseases related to the under-expression and over-expression of the amine transporter polypeptide and mutations in the nucleic acid sequences encoding such polypeptide.

In accordance with yet a further aspect of the present invention, there is provided a process for utilizing such polypeptides, or polynucleotides encoding such polypeptides, for in vitro purposes related to scientific research, synthesis of DNA and manufacture of DNA vectors.

These and other aspects of the present invention should be apparent to those skilled in the art from the teachings herein.

BRIEF DESCRIPTION OF THE FIGURES

The following drawings are illustrative of embodiments of the invention and are not meant to limit the scope of the invention as encompassed by the claims.

FIGS. 1A–1E illustrate the cDNA sequence (SEQ ID NO:1) and corresponding deduced amino acid sequence (SEQ ID NO:2) of the human amine transporter of the present invention. The standard one-letter abbreviations for amino acids are used. Sequencing was performed using a 373 Automated DNA sequencer (Applied Biosystems, Inc.). Sequencing accuracy is predicted to be greater than 97% accurate.

FIGS. 2A–2B illustrate an amino acid homology alignment between the amine transporter (SEQ ID NO:9) and a rat amine transporter (retrieved from Genbank public database).

DETAILED DESCRIPTION OF THE INVENTION

The amine transporter of the present invention may be responsible for re-uptake of one or any of the amine neurotransmitters present in mammalian cells. Examples of such amine transporters include dopamine, norepinephrine, epinephrine, serotonin and histamine, and other amino acid transmitters, including GABA, glycine and glutamate.

Figure 1C:
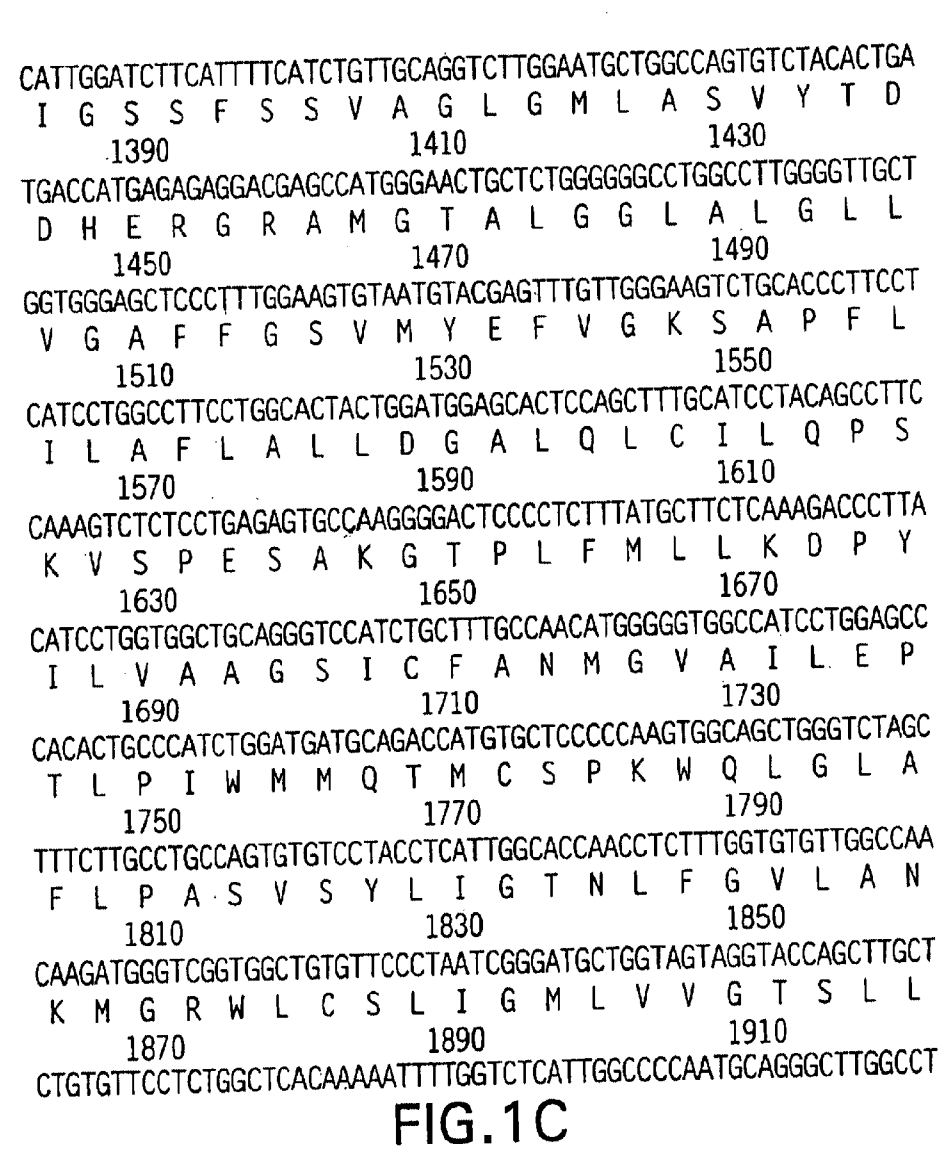

In accordance with an aspect of the present invention, there is provided an isolated nucleic acid (polynucleotide) which encodes for the mature polypeptide having the deduced amino acid sequence of FIGS. 1A–1E (SEQ ID No. 2) or for the mature polypeptide encoded by the cDNA of the clone deposited as ATCC Deposit No. 75980 on Dec. 16, 1994 at the American Type Culture Collection (ATCC), 10801 University Boulevard, Manassas Va. 20110-2209.

A polynucleotide encoding a polypeptide of the present invention may be obtained from a variety of human tissues. The polynucleotide of this invention was discovered in a cDNA library derived from a human adrenal gland tumor. It is structurally related to the amine transporter family. It contains an open reading frame encoding a protein of 470 amino acid residues. The protein exhibits the highest degree of homology to the rat amine transporter with 80% identity and 86% similarity over a 468 amino acid stretch.

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIGS. 1A–1E (SEQ ID No. 2) or that of the deposited clone or may be a different coding sequence which coding sequence, as a result of the redundancy or degeneracy of the genetic code, encodes the same mature polypeptide as the DNA of FIGS. 1A–1E (SEQ ID No. 2) or the deposited cDNA.

The polynucleotide which encodes for the mature polypeptide of FIGS. 1A–1E (SEQ ID No. 2) or for the mature polypeptide encoded by the deposited cDNA may include only the coding sequence for the mature polypeptide or the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIGS. 1A–1E (SEQ ID No. 2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIGS. 1A–1E (SEQ ID No. 2) or the same mature polypeptide encoded by the cDNA of the deposited clone as well as variants of such polynucleotides which variants encode for a fragment, derivative or analog of the polypeptide of FIGS. 1A–1E (SEQ ID No. 2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIGS. 1A–1E (SEQ ID No. 1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides of the present invention may also have the coding sequence fused in frame to a marker sequence which allows for purification of the polypeptide of the present invention. The marker sequence may be a hexa-histidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The term "gene" means the segment of DNA involved in producing a polypeptide chain; it includes regions preceding and following the coding region (leader and trailer) as well as intervening sequences (introns) between individual coding segments (exons).

Fragments of the full length gene of the present invention may be used as a hybridization probe for a cDNA library to isolate the full length cDNA and to isolate other cDNAs which have a high sequence similarity to the gene or similar biological activity. Probes of this type preferably have at least 30 bases and may contain, for example, 50 or more bases. The probe may also be used to identify a cDNA clone corresponding to a full length transcript and a genomic clone or clones that contain the complete gene including regulatory and promotor regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

The present invention further relates to polynucleotides which hybridize to the hereinabove-described sequences if there is at least 85%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIGS. 1A–1E (SEQ ID NO:1) or the deposited cDNA(s).

Alternatively, the polynucleotide may have at least 20 bases, preferably 30 bases, and more preferably at least 50 bases which hybridize to a polynucleotide of the present invention and which has an identity thereto, as hereinabove described, and which may or may not retain activity. For example, such polynucleotides may be employed as probes for the polynucleotide of SEQ ID NO:1, for example, for recovery of the polynucleotide or as a diagnostic probe or as a PCR primer.

Thus, the present invention is directed to polynucleotides having at least a 85% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a human amine transporter polypeptide which has the deduced amino acid sequence of FIGS. 1A–1E (SEQ ID No. 2) or which has the amino acid sequence encoded by the deposited cDNA, as well as fragments, analogs and derivatives of such polypeptide.

The terms "fragment," "derivative" and "analog" when referring to the polypeptide of FIGS. 1A–1E (SEQ ID No. 2) or that encoded by the deposited cDNA, means a polypeptide which retains essentially the same biological function or activity as such polypeptide. Thus, an analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

The fragment, derivative or analog of the polypeptide of FIGS. 1A–1E (SEQ ID No. 2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol). Such fragments, derivatives and analogs are deemed to be within the scope of those skilled in the art from the teachings herein.

The polypeptides and polynucleotides of the present invention are preferably provided in an isolated form, and preferably are purified to homogeneity.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The polypeptides of the present invention include the polypeptide of SEQ ID NO:2 (in particular the mature polypeptide) as well as polypeptides which have at least 80% similarity (preferably at least 70% identity) to the polypeptide of SEQ ID NO:2 and more preferably at least 90% similarity (more preferably at least 90% identity) to the polypeptide of SEQ ID NO:2 and still more preferably at least 95% similarity (still more preferably at least 90% identity) to the polypeptide of SEQ ID NO:2 and also include portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the human amine transporter genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila S2 and Spodoptera Sf9; animal cells such as CHO, HEK, COS or Bowes melanoma; adenoviruses; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pBS, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia). Eukaryotic: PWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are PKK232-8 and PCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HEK, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites may be used to provide the required nontranscribed genetic elements.

The human amine transporter polypeptide can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

Fragments of the full length human amine transporter gene may be used as a hybridization probe for a cDNA library to isolate the full length gene and to isolate other genes which have a high sequence similarity to the gene or similar biological activity. Probes of this type generally have at least 20 bases. Preferably, however, the probes have at least 30 bases and generally do not exceed 50 bases, although they may have a greater number of bases. The probe may also be used to identify a cDNA clone corresponding to a full length transcript and a genomic clone or clones that contain the complete human amine transporter gene including regulatory and promotor regions, exons, and introns. As an example of a screen comprises isolating the coding region of the human amine transporter gene by using the known DNA sequence to synthesize an oligonucleotide probe. Labeled oligonucleotides having a sequence complementary to that of the gene of the present invention are used to screen a library of human cDNA, genomic DNA or mRNA to determine which members of the library the probe hybridizes to.

This invention provides a method for determining amine neurotransmitters which are transported by the human amine transporter of the present invention. An example of an assay which will identify these neurotransmitters comprises infecting mammalian cells with recombinant vaccinia virus strain VTF-7 encoding a T7 RNA polymerase and following such infection with liposome-mediated transfection with the amine transporter gene through the use of a vector, for example, pBSSKII(−). Controlled transfections are also done with equivalent amounts of vector alone. Assays are performed eight hours following transfection in modified Krebs-Ringer-HEPES buffer. Cells are then incubated with [$^3$H] neurotransmitter (for example, GABA, dopamine, serotonin, etc.). Uptake is stopped by placing the cells on ice. Cells are solubilized in one percent SDS, and the amount of radioactivity accumulated is determined by liquid scintillation counting. A significant amount of uptake determines that the particular neurotransmitter is taken up by the human amine transporter of the present invention by determining background using control transfections with pBSSKII for each assay and subtracting the values obtained from the signals determined for the specific amine neurotransmitters.

This invention also provides a method of detecting expression of an amine transporter on the surface of a cell by detecting the presence of mRNA coding for an amine transporter. This method comprises obtaining total mRNA from the cell using methods well-known in the art and contacting the mRNA so obtained with a nucleic acid probe of at least 15 nucleotides and which is capable of specifically hybridizing with a sequence included within the sequence of a nucleic acid molecule encoding a human amine transporter, under hybridizing conditions, detecting the presence of mRNA hybridized to the probe, and thereby detecting the expression of the amine transporter by the cell. Hybridization of probes to target nucleic acid molecules such as mRNA molecules employs techniques well known in the art. However, in one embodiment of this invention, nucleic acids are extracted by precipitation from lysed cells and the mRNA is isolated from the extract using a column which binds the poly-A tails of the mRNA molecules. The mRNA is then exposed to radioactively labelled probe on a nitrocellulose membrane, and the probe hybridizes to and thereby labels complementary mRNA sequences. Binding may be detected by autoradiography or scintillation counting. However, other methods for performing these steps are well known to those of skill in the art.

Alternatively, an antibody directed to the human amine transporter may be employed under conditions permitting binding of the antibody to the transporter, and detecting the presence of the transporter on the surface of the cell. Such a method may be employed for determining whether a given cell is defective in expression of the amine transporter. Detection methods include fluorescent markers bound to the antibodies.

The invention also provides a method for determining whether a compound not known to be capable of specifically binding to a human amine transporter can specifically bind to the human amine transporter, which comprises contacting a mammalian cell comprising a plasmid adapted for expression in a mammalian cell which plasmid further comprises a DNA which expresses the amine transporter on the cell surface with the compound under conditions permitting binding of ligands known to bind to the amine transporter, detecting the presence of any compound bound to the mammalian amine transporter, the presence of bound compound indicating that the compound is capable of specifically binding to the human amine transporter.

This invention also provides a method of screening drugs to identify drugs which specifically interact with, and bind to a human amine transporter on the surface of a cell which comprises contacting a mammalian cell which expresses the human amine transporter on the surface of a cell with a plurality of drugs, detecting those drugs which bind to the cell, and thereby identifying drugs which specifically interact with, and bind to, the human amine transporter.

The present invention further provides a method for identifying agonist or antagonist compounds to the human amine transporter of the present invention by the employment of competition assays. An example of such an assay for identifying antagonists comprises contacting a neuronal cell which expresses the human amine transporter on the surface thereof with a known neurotransmitter, in the presence of a potential compound to determine the amount of neurotransmitter transported. Controls may also be prepared in the absence of the potential compound and the amount of amine neurotransmitter transported by the cell upon comparison to the control cell indicates if the potential compound stimulated transport or inhibited transport of the labeled amine neurotransmitter by the transfected mammalian cell.

Examples of human amine transporter antagonists include an antibody directed to the human amine transporter which comprises, for example, a monoclonal antibody directed to an epitope of a human amine transporter present on the surface of the cell. These antibodies are useful to detect the presence of human amine transporters or to inhibit the function of the transporters in humans.

Another potential antagonist is an antisense construct prepared using antisense technology. Antisense technology can be used to control gene expression through triple-helix formation or antisense DNA or RNA, both of which methods are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of human amine transporter. The antisense RNA oligonucleotide hybridizes to the mRNA in vivo and blocks translation of the mRNA molecule into the human amine transporter polypeptide (antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells such that the antisense RNA or DNA may be expressed in vivo to inhibit production of human amine transporter.

Potential antagonists also include a soluble form of a human amine transporter, e.g. a fragment of the transporter, which binds to the neurotransmitter and prevents it from interacting with the human amine transporter.

Potential antagonists further include a small molecule which binds to and occupies the extracellular portion of the human amine transporter thereby making the human amine transporter inaccessible to the neurotransmitter such that transport is inhibited. Examples of small molecules include but are not limited to small peptides or peptide-like molecules.

This invention additionally provides a method of treating an abnormal condition related to an excess of amine transporter activity which comprises administering to a subject the antagonist as hereinabove described along with a pharmaceutically acceptable carrier in an amount effective to block binding of naturally occurring substrates to the amine transporters and thereby alleviate the abnormal condition. Examples of abnormal conditions include epilepsy, schizophrenia, depression, cognitive impairment, anxiety and migraine headaches.

The invention also provides a method of treating abnormal conditions related to an under-expression of amine transporter activity which comprises administering to a subject an amount of the agonist described above in combination with a pharmaceutically acceptable carrier, in an amount effective to enhance binding of naturally occurring substrates to the amine transporter and thereby alleviate the abnormal conditions. Some examples of abnormal conditions are Parkinson's disease and Alzheimer's disease.

The soluble form of the human amine transporter, and agonists and antagonists may be employed in combination with a suitable pharmaceutical carrier. Such compositions comprise a therapeutically effective amount of the transporter, agonist or antagonist and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions may be employed in conjunction with other therapeutic compounds.

The pharmaceutical compositions may be administered in a convenient manner such as by the oral, topical, intravenous, intraperitoneal, intramuscular, subcutaneous, intranasal or intradermal routes. The pharmaceutical compositions are administered in an amount which is effective for treating and/or prophylaxis of the specific indication. In general, they are administered in an amount of at least about 10 $\mu$g/kg body weight and in most cases they will be administered in an amount not in excess of about 8 mg/Kg body weight per day. In most cases, the dosage is from about 10 $\mu$g/kg to about 1 mg/kg body weight daily, taking into account the routes of administration, symptoms, etc.

The human amine transporter and agonists and antagonists which are polypeptides may also be employed in accordance with the present invention by expression of such polypeptides in vivo, which is often referred to as "gene therapy."

Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., *Biotechniques*, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, ψ-2, ψ-AM, PA12, T19-14X, VT-19-17-H2, ψCRE, ψCRIP, GP+E-86, GP+envAm12, and DAN cell lines as described in Miller, *Human Gene Therapy*, Vol. 1, pgs. 5–14 (1990), which is incorporated herein by reference in its entirety. The vector may transduce the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention is also related to the use of the human amine transporter gene as part of a diagnostic assay for detecting diseases or susceptibility to diseases related to the presence of mutations in the human amine transporter genes. Such diseases are related to under-expression of the human amine transporter.

Individuals carrying mutations in the human amine transporter gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR (Saiki et al., Nature, 324:163–166 (1986)) prior to analysis. RNA or cDNA may also be used for the same purpose. As an example, PCR primers complementary to the nucleic acid encoding the human amine transporter protein can be used to identify and analyze human amine transporter mutations. For example, deletions and insertions can be detected by a change in size of the amplified product in comparison to the normal genotype. Point mutations can be identified by hybridizing amplified DNA to radiolabeled human amine transporter RNA or alternatively, radiolabeled human amine transporter antisense DNA sequences. Perfectly matched sequences can be distinguished from mismatched duplexes by RNase A digestion or by differences in melting temperatures.

Genetic testing based on DNA sequence differences may be achieved by detection of alteration in electrophoretic mobility of DNA fragments in gels with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., Science, 230:1242 (1985)).

Sequence changes at specific locations may also be revealed by nuclease protection assays, such as RNase and S1 protection or the chemical cleavage method (e.g., Cotton et al., PNAS, USA, 85:4397–4401 (1985)).

Thus, the detection of a specific DNA sequence may be achieved by methods such as hybridization, RNase protection, chemical cleavage, direct DNA sequencing or the use of restriction enzymes, (e.g., Restriction Fragment Length Polymorphisms (RFLP)) and Southern blotting of genomic DNA.

In addition to more conventional gel-electrophoresis and DNA sequencing, mutations can also be detected by in situ analysis.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., Human Chromosomes: a Manual of Basic Techniques, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units of T4 DNA ligase ("ligase") per 0.5 μg of approximately equimolar amounts of the DNA fragments to be ligated.

Unless otherwise stated, transformation was performed as described in the method of Graham, F. and Van der Eb, A., Virology, 52:456–457 (1973).

EXAMPLES

Example 1

Bacterial Expression and Purification of Human Amine Transporter

The DNA sequence encoding human amine transporter, ATCC #75980, is initially amplified using PCR oligonucleotide primers corresponding to the 5' and 3' end sequences of the processed amine transporter nucleic acid sequence (minus the signal peptide sequence). Additional nucleotides corresponding to amine transporter gene are added to the 5' and 3' sequences respectively. The 5' oligonucleotide primer has the sequence 5' GACTAAAGCTTAATGCTCCGGC-CCATTCTG 3' (SEQ ID No. 3) contains a HindIII restriction enzyme site followed by 18 nucleotides of human amine transporter coding sequence starting from the presumed terminal amino acid of the processed protein. The 3' sequence 5' GAACTTCTAGACGGTCAGCCATGGT-GACTGG 3' (SEQ ID No. 4) contains complementary sequences to an XbaI site and is followed by 20 nucleotides of the human amine transporter gene. The restriction enzyme sites correspond to the restriction enzyme sites on the bacterial expression vector pQE-9 (Qiagen, Inc. Chatsworth, Calif.). pQE-9 encodes antibiotic resistance (Amp$^r$), a bacterial origin of replication (ori), an IPTG-regulatable promoter operator (P/O), a ribosome binding site (RBS), a 6-His tag and restriction enzyme sites. pQE-9 is then digested with HindIII and XbaI. The amplified sequences are ligated into pQE-9 and are inserted in frame with the sequence encoding for the histidine tag and the RBS. The ligation mixture is then used to transform E. coli strain M15/rep 4 (Qiagen, Inc.) by the procedure described in Sambrook, J. et al., Molecular Cloning: A Laboratory Manual, Cold Spring Laboratory Press, (1989). M15/rep4 contains multiple copies of the plasmid pREP4, which expresses the laci repressor and also confers kanamycin resistance (Kan$^r$). Transformants are identified by their ability to grow on LB plates and ampicillin/kanamycin resistant colonies are selected. Plasmid DNA is isolated and confirmed by restriction analysis. Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.$^{600}$) of between 0.4 and 0.6. IPTG ("Isopropyl-B-D-thiogalacto pyranoside") is then added to a final concentration of 1 mM. IPTG induces by inactivating the laci repressor, clearing the P/O leading to increased gene expression. Cells are grown an extra 3 to 4 hours. Cells are then harvested by centrifugation. The cell pellet is solubilized in the chaotropic agent 6 Molar Guanidine HCl. After clarification, solubilized human amine transporter is purified from this solution by chromatography on a Nickel-Chelate column under conditions that allow for tight binding by proteins containing the 6-His tag (Hochuli, E. et al., J. Chromatography 411:177–184 (1984)). Human amine transporter protein is eluted from the column in 6 molar guanidine HCl pH. 5.0 and for the purpose of renaturation adjusted to 3 molar guanidine HCl, 100 mM sodium phosphate, 10 mmolar glutathione (reduced) and 2 mmolar glutathione (oxidized). After incubation in this solution for 12 hours the protein is dialyzed to 10 mmolar sodium phosphate.

Example 2

Cloning and Expression of Human Amine Transporter Using the Baculovirus Expression System The DNA sequence encoding the full length human amine transporter protein, ATCC #75980, is amplified using PCR oligonucleotide primers corresponding to the 5' and 3' sequences of the gene:

The 5' primer has the sequence 5' CGGGATCCCTC-CATGGCT CCGGCCCATTCTG 3' (SEQ ID No. 5) and contains a BamHI restriction enzyme site (in bold) followed by 4 nucleotides resembling an efficient signal for the initiation of translation in eukaryotic cells (Kozak, M., J. Mol. Biol., 196:947–950 (1987) which is just behind the first 18 nucleotides of the human amine transporter gene (the initiation codon for translation "ATG" is underlined).

The 3' primer has the sequence 5' CGGGATCCCGCT CAGCCATGGTGACTGGT 3' (SEQ ID No. 6) and contains the cleavage site for the restriction endonuclease BamHI and 18 nucleotides complementary to the 3' non-translated sequence of the human amine transporter gene. The amplified sequences are isolated from a 1% agarose gel using a commercially available kit ("Geneclean," BIO 101 Inc., La Jolla, Calif.). The fragment is then digested with the endonucleases BamHI and then purified again on a 1% agarose gel. This fragment is designated F2.

The vector pRG1 (modification of pVL941 vector, discussed below) is used for the expression of the human amine transporter protein using the baculovirus expression system (for review see: Summers, M. D. and Smith, G. E. 1987, A manual of methods for baculovirus vectors and insect cell culture procedures, Texas Agricultural Experimental Station Bulletin No. 1555). This expression vector contains the strong polyhedrin promoter of the Autographa californica nuclear polyhedrosis virus (AcMNPV) followed by the recognition sites for the restriction endonucleases BamHI. The polyadenylation site of the simian virus (SV)40 is used for efficient polyadenylation. For an easy selection of recombinant viruses the beta-galactosidase gene from E.coli is inserted in the same orientation as the polyhedrin promoter followed by the polyadenylation signal of the polyhedrin gene. The polyhedrin sequences are flanked at both sides by viral sequences for the cell-mediated homologous recombination of co-transfected wild-type viral DNA. Many other baculovirus vectors could be used in place of pRG1 such as pAc373, pVL941 and pAcIM1 (Luckow, V. A. and Summers, M. D., Virology, 170:31–39).

The plasmid is digested with the restriction enzymes BamHI and then dephosphorylated using calf intestinal phosphatase by procedures known in the art. The DNA is then isolated from a 1% agarose gel using the commercially available kit ("Geneclean" BIO 101 Inc., La Jolla, Calif.). This vector DNA is designated V2.

Fragment F2 and the dephosphorylated plasmid V2 are ligated with T4 DNA ligase. *E.coli* HB101 cells are then transformed and bacteria identified that contained the plasmid (pBac-Human amine transporter) with the human amine transporter gene using the enzyme BamHI. The sequence of the cloned fragment is confirmed by DNA sequencing.

5 μg of the plasmid pBac-Human amine transporter is co-transfected with 1.0 μg of a commercially available linearized baculovirus ("BaculoGold™ baculovirus DNA", Pharmingen, San Diego, Calif.) using the lipofection method (Felgner et al. Proc. Natl. Acad. Sci. USA, 84:7413–7417 (1987)).

1 μg of BaculoGold™ virus DNA and 5 μg of the plasmid pBac-Human amine transporter are mixed in a sterile well of a microtiter plate containing 50 μl of serum free Grace's medium (Life Technologies Inc., Gaithersburg, Md.). Afterwards 10 μl Lipofectin plus 90 μl Grace's mediuti are added, mixed and incubated for 15 minutes at room temperature. Then the transfection mixture is added drop-wise to the Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation continued at 27° C. for four days.

After four days the supernatant is collected and a plaque assay performed similar as described by Summers and Smith (supra). As a modification an agarose gel with "Blue Gal" (Life Technologies Inc., Gaithersburg) is used which allows an easy isolation of blue stained plaques. (A detailed description of a "plaque assay" can also be found in the user's guide for insect cell culture and baculovirology distributed by Life Technologies Inc., Gaithersburg, page 9–10).

Four days after the serial dilution, the viruses are added to the cells and blue stained plaques are picked with the tip of an Eppendorf pipette. The agar containing the recombinant viruses is then resuspended in an Eppendorf tube containing 200 μl of Grace's medium. The agar is removed by a brief centrifugation and the supernatant containing the recombinant baculovirus is used to infect Sf9 cells seeded in 35 mm dishes. Four days later the supernatants of these culture dishes are harvested and then stored at 4° C.

Sf9 cells are grown in Grace's medium supplemented with 10% heat-inactivated FBS. The cells are infected with the recombinant baculovirus V-Human amine transporter at a multiplicity of infection (MOI) of 2. Six hours later the medium is removed and replaced with SF900 II medium minus methionine and cysteine (Life Technologies Inc., Gaithersburg). 42 hours later 5 μCi of $^{35}$S-methionine and 5 μCi $^{35}$S cysteine (Amersham) are added. The cells are further incubated for 16 hours before they are harvested by centrifugation and the labelled proteins visualized by SDS-PAGE and autoradiography.

Example 3

Expression of Recombinant Human Amine Transporter in COS Cells

The expression of plasmid, Human amine transporter HA is derived from a vector pcDNAI/Amp (Invitrogen) containing: 1) SV40 origin of replication, 2) ampicillin resistance gene, 3) *E.coli* replication origin, 4) CMV promoter followed by a polylinker region, a SV40 intron and polyadenylation site. A DNA fragment encoding the entire Human amine transporter precursor and a HA tag fused in frame to its 3' end is cloned into the polylinker region of the vector, therefore, the recombinant protein expression is directed under the CMV promoter. The HA tag correspond to an epitope derived from the influenza hemagglutinin protein as previously described (I. Wilson, et al., Cell, 37:767, (1984)). The infusion of HA tag to the target protein allows easy detection of the recombinant protein with an antibody that recognizes the HA epitope.

The plasmid construction strategy is described as follows:

The DNA sequence encoding Human amine transporter, ATCC #75980, is constructed by PCR using two primers: the 5 primer 5' GTCCAAGCTTGCCACCATGCTGCGGC-CCATTCTG 3' (SEQ ID No. 7) contains a HindIII site followed by 18 nucleotides of Human amine transporter coding sequence starting from the initiation codon; the 3' sequence 5' CTAGCTCGAGTCAGCCATGG TGACTGG-TAGCGTAGTCTGGGACGTCGTATGGGTAGCA 3' (SEQ ID No. 8) contains complementary sequences to an XhoI site, translation stop codon, HA tag and the last 18 nucleotides of the Human amine transporter coding sequence (not including the stop codon). Therefore, the PCR product contains a HindIII site, human amine transporter coding sequence followed by HA tag fused in frame, a translation termination stop codon next to the HA tag, and an HindIII site. The PCR amplified DNA fragment and the vector, pcDNAI/Amp, are digested with HindIII and XhoI restriction enzyme and ligated. The ligation mixture is transformed into *E. coli* strain SURE (Stratagene Cloning Systems, La Jolla, Calif.) the transformed culture is plated on ampicillin media plates and resistant colonies are selected. Plasmid DNA is isolated from transformants and examined by restriction analysis for the presence of the correct fragment. For expression of the recombinant amine transporter, COS cells are transfected with the expression vector by DEAE-DEXTRAN method (J. Sambrook, E. Fritsch, T. Maniatis, Molecular Cloning: A Laboratory Manual, Cold Spring Laboratory Press, (1989)). The expression of the Human amine transporter HA protein is detected by radiolabelling and immunoprecipitation method (E. Harlow, D. Lane, Antibodies: A Laboratory Manual, Cold Spring Harbor Laboratory Press, (1988)). Cells are labelled for 8 hours with $^{35}$S-cysteine two days post transfection. Culture media is then collected and cells are lysed with detergent (RIPA buffer (150 mM NaCl, 1% NP-40, 0.1% SDS, 1% NP-40, 0.5% DOC, 50 mM Tris, pH 7.5) (Wilson, I. et al., Id. 37:767 (1984)). Both cell lysate and culture media are precipitated with a HA specific monoclonal antibody. Proteins precipitated are analyzed on 15% SDS-PAGE gels.

Example 4

Expression Pattern of Human Amine Transporter in Human Tissue

Northern blot analysis is carried out to examine the levels of expression of Human amine transporter in human tissues. Total cellular RNA samples are isolated with RNAzol™ B system .(Biotecx Laboratories, Inc. Houston, Tex.). About 10 μg of total RNA isolated from each human tissue specified is separated on 1% agarose gel and blotted onto a nylon filter (Sambrook, Fritsch, and Maniatis, Molecular Cloning, Cold Spring Harbor Press, (1989)). The labeling reaction is done according to the Stratagene Prime-It kit with 50ng DNA fragment. The labeled DNA is purified with a Select-G-50 column (5 Prime-3 Prime, Inc. Boulder, Colo.). The filter is then hybridized with radioactive labeled full length Human amine transporter gene at 1,000,000 cpm/ml in 0.5 M $NaPO_4$, pH 7.4 and 7% SDS overnight at 65° C. After wash twice at room temperature and twice at 60° C. with 0.5×SSC, 0.1% SDS, the filter is then exposed at −70° C. overnight with an intensifying screen.

Example 4

Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer $further includes a HindIII site. Equal quantities of the Moloney murine sarcoma virus linear backbone and the amplified $EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. A method of producing an antibody which specifically binds the polypeptide of SEQ ID NO:2 comprising:
   (a) introducing a polypeptide consisting of at least 50 contiguous amino acids of SEQ ID NO:2 into an animal; and
   (b) recovering said antibody from said animal.

2. The method of claim 1 wherein the antibody specifically binds the polypeptide of SEQ ID NO:2 expressed on the surface of a cell.

3. A method of producing an antibody which specifically binds the polypeptide encoded by the human cDNA in ATCC Deposit No. 75980 comprising:
   (a) introducing a polypeptide consisting of at least 50 contiguous amino acids encoded by ATCC Deposit No. 75980 into an animal; and
   (b) recovering said antibody from said animal.

4. The method of claim 3 wherein the antibody specifically binds the polypeptide encoded by the human cDNA in ATCC Deposit No. 75980 expressed on the surface of a cell.

5. A method of producing an antibody which specifically binds the polypeptide of SEQ ID NO:2 comprising:
   (a) screening a single chain or Fab expression library to identify an antibody which specifically binds the polypeptide of SEQ ID NO:2; and
   (b) recovering said antibody from said library.

6. The method of claim 5 wherein the antibody is a single chain antibody.

7. The method of claim 5 wherein the antibody is an Fab fragment.

8. The method of claim 5 wherein the antibody specifically binds the polypeptide of SEQ ID NO:2 expressed on the surface of a cell.

9. A method of producing an antibody which specifically binds the polypeptide encoded by the human cDNA in ATCC Deposit No. 75980 comprising:
   (a) screening a single chain or Fab expression library to identify an antibody which specifically binds the polypeptide encoded by the human cDNA in ATCC Deposit No. 75980; and
   (b) recovering said antibody from said library.

10. The method of claim 9 wherein the antibody is a single chain antibody.

11. The method of claim 9 wherein the antibody is an Fab fragment.

12. The method of claim wherein the antibody specifically binds the polypeptide encoded by the human cDNA in ATCC Deposit No. 75980 expressed on the surface of a cell.

* * * * *

SEQUENCE LISTING

```
<160> NUMBER OF SEQ ID NOS: 9

<210> SEQ ID NO 1
<211> LENGTH: 2885
<212> TYPE: DNA
<213> ORGANISM: Homo sapiens
<220> FEATURE:
<221> NAME/KEY: CDS
<222> LOCATION: (719)..(2128)
<220> FEATURE:
<221> NAME/KEY: UNSURE
<222> LOCATION: (39)
<223> OTHER INFORMATION: May be any nucleic acid
<220> FEATURE:
<221> NAME/KEY: UNSURE
<222> LOCATION: (67)
<223> OTHER INFORMATION: May be any nucleic acid
<220> FEATURE:
<221> NAME/KEY: UNSURE
<222> LOCATION: (70)
<223> OTHER INFORMATION: May be any nucleic acid
<220> FEATURE:
<221> NAME/KEY: UNSURE
<222> LOCATION: (409)
<223> OTHER INFORMATION: May be any nucleic acid
```

-continued

```
<220> FEATURE:
<221> NAME/KEY: UNSURE
<222> LOCATION: (437)
<223> OTHER INFORMATION: May be any nucleic acid
<220> FEATURE:
<221> NAME/KEY: UNSURE
<222> LOCATION: (1922)
<223> OTHER INFORMATION: May be any nucleic acid
<220> FEATURE:
<221> NAME/KEY: UNSURE
<222> LOCATION: (2587)
<223> OTHER INFORMATION: May be any nucleic acid
<220> FEATURE:
<221> NAME/KEY: UNSURE
<222> LOCATION: (2687)
<223> OTHER INFORMATION: May be any nucleic acid
<220> FEATURE:
<221> NAME/KEY: UNSURE
<222> LOCATION: (2735)
<223> OTHER INFORMATION: May be any nucleic acid
<220> FEATURE:
<221> NAME/KEY: UNSURE
<222> LOCATION: (2751)
<223> OTHER INFORMATION: May be any nucleic acid
<220> FEATURE:
<221> NAME/KEY: UNSURE
<222> LOCATION: (2761)
<223> OTHER INFORMATION: May be any nucleic acid
<220> FEATURE:
<221> NAME/KEY: UNSURE
<222> LOCATION: (2763)
<223> OTHER INFORMATION: May be any nucleic acid
<220> FEATURE:
<221> NAME/KEY: UNSURE
<222> LOCATION: (2771)
<223> OTHER INFORMATION: May be any nucleic acid
<220> FEATURE:
<221> NAME/KEY: UNSURE
<222> LOCATION: (2792)
<223> OTHER INFORMATION: May be any nucleic acid

<400> SEQUENCE: 1
tcctgcgtta tccccctgat tctgtggata accgtattnc cgcctttgag tgagctgata      60
ccgctcnccn cagccgaacg accgagcgca gcgagtcagt gagcgaggaa gcggaagagc     120
gcccaatacg caaaccgcct ctccccgcgc gttggccgat tcattaatgc agctggcacg     180
acaggtttcc cgactggaaa gcgggcagtg agcgcaacgc aattaatgtg agttagctca     240
ctcattaggc accccaggct ttacacttta tgcttccggc tcgtatgttg tgtggaattg     300
tgagcggata caatttcac acaggaaaca gctatgacca tgattacgcc aagctcgaaa      360
ttaaccctca ctaaagggaa caaaagctgg agctccaccg cggtggcgnc cgctctagaa     420
ctagtggatc ccccggnctg caggggcaca cacacgcaca catacacaga atcctcagat     480
aacaggaggc aataaatcca acagcacatc cacgttcaga gaacagtgtc cctgctgtct     540
tgctaacagc tgccaatacc tcactgagtg cctcacacca acatgggctc caagtgagtt     600
tcattcgtct gggcagactc cctcccctct tccataaagg ctgcaggaga cctgtagctg     660
tcacaggacc ttccctaaga gcccgcaggg ggaagactgc cccagtccgg ccatcacc       718 atg ctc cgg ccc att ctg gat gct ccc cag cgg ttg ctg aag gag ggg      766
Met Leu Arg Pro Ile Leu Asp Ala Pro Gln Arg Leu Leu Lys Glu Gly
  1               5                  10                  15 aga gcg tcc cgg cag ctg gtg ctg gtg gtg gta ttc gtc gct ttg ctc      814
Arg Ala Ser Arg Gln Leu Val Leu Val Val Val Phe Val Ala Leu Leu
             20                  25                  30 ctg gac aac atg ctg ttt act gtg gtg gtg cca att gtg ccc acc ttc      862
Leu Asp Asn Met Leu Phe Thr Val Val Val Pro Ile Val Pro Thr Phe
         35                  40                  45
```

-continued

| | |
|---|---|
| cta tat gac atg gag ttc aaa gaa gtc atc tct tct ctg cac ctc ggg<br>Leu Tyr Asp Met Glu Phe Lys Glu Val Ile Ser Ser Leu His Leu Gly<br>50                        55                       60 | 910 |
| cat gcc gga agt tcc cca cat gcc ctc gcc tct cct gcc ttt tcc acc<br>His Ala Gly Ser Ser Pro His Ala Leu Ala Ser Pro Ala Phe Ser Thr<br>65                        70                       75                       80 | 958 |
| atc ttc tcc ttc ttc aac aac aac acc gtg gct gtt gaa gaa agc gta<br>Ile Phe Ser Phe Phe Asn Asn Asn Thr Val Ala Val Glu Glu Ser Val<br>                      85                       90                       95 | 1006 |
| cct agt gga ata gca tgg atg aat gac act gcc agc acc atc cca cct<br>Pro Ser Gly Ile Ala Trp Met Asn Asp Thr Ala Ser Thr Ile Pro Pro<br>               100                     105                     110 | 1054 |
| cca gcc act gaa gcc atc tca gct cat aaa aac aac tgc ttg caa ggc<br>Pro Ala Thr Glu Ala Ile Ser Ala His Lys Asn Asn Cys Leu Gln Gly<br>               115                     120                     125 | 1102 |
| aca ggt ttc ttg gag gaa gag act acc cgg gtc ggg gtt ctg ttt gct<br>Thr Gly Phe Leu Glu Glu Glu Thr Thr Arg Val Gly Val Leu Phe Ala<br>130                       135                     140 | 1150 |
| tca aag gct gtg atg caa ctt ctg gtc aac cca ttc gtg ggc cct ctc<br>Ser Lys Ala Val Met Gln Leu Leu Val Asn Pro Phe Val Gly Pro Leu<br>145                       150                     155                 160 | 1198 |
| acc aac agg att gga tat cat atc ccc atg ttt gct ggc ttt gtt atc<br>Thr Asn Arg Ile Gly Tyr His Ile Pro Met Phe Ala Gly Phe Val Ile<br>               165                     170                     175 | 1246 |
| atg ttt ctc tcc aca gtt atg ttt gct ttt tct ggg acc tat act cta<br>Met Phe Leu Ser Thr Val Met Phe Ala Phe Ser Gly Thr Tyr Thr Leu<br>               180                     185                     190 | 1294 |
| ctc ttt gtg gcc cga acc ctt caa ggc att gga tct tca ttt tca tct<br>Leu Phe Val Ala Arg Thr Leu Gln Gly Ile Gly Ser Ser Phe Ser Ser<br>               195                     200                     205 | 1342 |
| gtt gca ggt ctt gga atg ctg gcc agt gtc tac act gat gac cat gag<br>Val Ala Gly Leu Gly Met Leu Ala Ser Val Tyr Thr Asp Asp His Glu<br>210                       215                     220 | 1390 |
| aga gga cga gcc atg gga act gct ctg ggg ggc ctg gcc ttg ggg ttg<br>Arg Gly Arg Ala Met Gly Thr Ala Leu Gly Gly Leu Ala Leu Gly Leu<br>225                       230                     235                     240 | 1438 |
| ctg gtg gga gct ccc ttt gga agt gta atg tac gag ttt gtt ggg aag<br>Leu Val Gly Ala Pro Phe Gly Ser Val Met Tyr Glu Phe Val Gly Lys<br>               245                     250                     255 | 1486 |
| tct gca ccc ttc ctc atc ctg gcc ttc ctg gca cta ctg gat gga gca<br>Ser Ala Pro Phe Leu Ile Leu Ala Phe Leu Ala Leu Leu Asp Gly Ala<br>               260                     265                     270 | 1534 |
| ctc cag ctt tgc atc cta cag cct tcc aaa gtc tct cct gag agt gcc<br>Leu Gln Leu Cys Ile Leu Gln Pro Ser Lys Val Ser Pro Glu Ser Ala<br>               275                     280                     285 | 1582 |
| aag ggg act ccc ctc ttt atg ctt ctc aaa gac cct tac atc ctg gtg<br>Lys Gly Thr Pro Leu Phe Met Leu Leu Lys Asp Pro Tyr Ile Leu Val<br>               290                     295                     300 | 1630 |
| gct gca ggg tcc atc tgc ttt gcc aac atg ggg gtg gcc atc ctg gag<br>Ala Ala Gly Ser Ile Cys Phe Ala Asn Met Gly Val Ala Ile Leu Glu<br>305                       310                     315                     320 | 1678 |
| ccc aca ctg ccc atc tgg atg atg cag acc atg tgc tcc ccc aag tgg<br>Pro Thr Leu Pro Ile Trp Met Met Gln Thr Met Cys Ser Pro Lys Trp<br>               325                     330                     335 | 1726 |
| cag ctg ggt cta gct ttc ttg cct gcc agt gtg tcc tac ctc att ggc<br>Gln Leu Gly Leu Ala Phe Leu Pro Ala Ser Val Ser Tyr Leu Ile Gly<br>               340                     345                     350 | 1774 |
| acc aac ctc ttt ggt gtg ttg gcc aac aag atg ggt cgg tgg ctg tgt<br>Thr Asn Leu Phe Gly Val Leu Ala Asn Lys Met Gly Arg Trp Leu Cys<br>355                       360                     365 | 1822 |

```
tcc cta atc ggg atg ctg gta gta ggt acc agc ttg ctc tgt gtt cct        1870
Ser Leu Ile Gly Met Leu Val Val Gly Thr Ser Leu Leu Cys Val Pro
    370                 375                 380 ctg gct cac aaa aat ttt ggt ctc att ggc ccc aat gca ggg ctt ggc        1918
Leu Ala His Lys Asn Phe Gly Leu Ile Gly Pro Asn Ala Gly Leu Gly
385                 390                 395                 400 ctt ncc ata ggc atg gtg gaa tct tct atg atg ccc atc atg ggg cac        1966
Leu Xaa Ile Gly Met Val Glu Ser Ser Met Met Pro Ile Met Gly His
                405                 410                 415 ctg gtg gat cca cgc cac acc tcg gtg tat ggg agt gtc cac gcc atc        2014
Leu Val Asp Pro Arg His Thr Ser Val Tyr Gly Ser Val His Ala Ile
            420                 425                 430 gct gat gtg gct ttt tgc atg ggc ttt gct ata ggc tat tct gag tca        2062
Ala Asp Val Ala Phe Cys Met Gly Phe Ala Ile Gly Tyr Ser Glu Ser
        435                 440                 445 gga ctg ccc cat gga gac ccg gat gta tca acc cag aaa cct ctt ccc        2110
Gly Leu Pro His Gly Asp Pro Asp Val Ser Thr Gln Lys Pro Leu Pro
    450                 455                 460 tgg acc agt cac cat ggc tgacccacgg ctcagtggcc tcaaaacctc               2158
Trp Thr Ser His His Gly
465                 470 tgcctgggat cttcttcctc ccctcccatg gagactgtcc ctcatactct tctcacctgt      2218
gtaacttgta gctcttcmtc tatgccttgg tgccgcagtg gcccatcttt tatgggaaga      2278
cagagtgatg caccyycccg ctgctgtgag gttgattaaa cttgagctgt gacggggttc      2338 tgcaagggt gactcattgy atagaggtgg tagtgagtaa tgtgcccctg aaaccagtgg       2398
ggtgactgac aagcctcttt aatctgttgc ctgattttct ctggcatagc cccaacagat     2458
cggaagagtg ttaccctctt twccctcaac gtgttctttc ccgggttttc cccagccgag      2518
ttgagaaaat gttctcagca ttgtcttgct gccaaatgcc agcktgaaga gttwggtatg      2578
ktttttctnc catttatttt atttattwac taaagtgaat gattttactg tggytaaatc      2638
tagagctgct aaaagggctt taccctcagt gaaaagtgtc ttctatttnc atwatctttc      2698
agaaacwgga gcccatttct cttctggtgg agttatngac atcctcctga ccnccctgt       2758 gtntncctac ctntactgaa cctcttagac tctnagaaat aaaagtagaa gaaagacaga      2818
aaaattaact gattagaccc aagatttcat gggaagaagt taaagaaac tgccttggaa       2878 atccctc                                                                 2885
```

<210> SEQ ID NO 2
<211> LENGTH: 470
<212> TYPE: PRT
<213> ORGANISM: Homo sapiens
<220> FEATURE:
<221> NAME/KEY: UNSURE
<222> LOCATION: (402)
<223> OTHER INFORMATION: May be any amino acid

<400> SEQUENCE: 2

```
Met Leu Arg Pro Ile Leu Asp Ala Pro Gln Arg Leu Leu Lys Glu Gly
1               5                   10                  15

Arg Ala Ser Arg Gln Leu Val Leu Val Val Phe Val Ala Leu Leu
            20                  25                  30

Leu Asp Asn Met Leu Phe Thr Val Val Pro Ile Val Pro Thr Phe
        35                  40                  45

Leu Tyr Asp Met Glu Phe Lys Glu Val Ile Ser Ser Leu His Leu Gly
    50                  55                  60
```

-continued

His Ala Gly Ser Ser Pro His Ala Leu Ala Ser Pro Ala Phe Ser Thr
 65                  70                  75                  80

Ile Phe Ser Phe Phe Asn Asn Asn Thr Val Ala Val Glu Glu Ser Val
                 85                  90                  95

Pro Ser Gly Ile Ala Trp Met Asn Asp Thr Ala Ser Thr Ile Pro Pro
            100                 105                 110

Pro Ala Thr Glu Ala Ile Ser Ala His Lys Asn Asn Cys Leu Gln Gly
        115                 120                 125

Thr Gly Phe Leu Glu Glu Thr Thr Arg Val Gly Val Leu Phe Ala
    130                 135                 140

Ser Lys Ala Val Met Gln Leu Leu Val Asn Pro Phe Val Gly Pro Leu
145                 150                 155                 160

Thr Asn Arg Ile Gly Tyr His Ile Pro Met Phe Ala Gly Phe Val Ile
                165                 170                 175

Met Phe Leu Ser Thr Val Met Phe Ala Phe Ser Gly Thr Tyr Thr Leu
            180                 185                 190

Leu Phe Val Ala Arg Thr Leu Gln Gly Ile Gly Ser Ser Phe Ser Ser
        195                 200                 205

Val Ala Gly Leu Gly Met Leu Ala Ser Val Tyr Thr Asp Asp His Glu
    210                 215                 220

Arg Gly Arg Ala Met Gly Thr Ala Leu Gly Gly Leu Ala Leu Gly Leu
225                 230                 235                 240

Leu Val Gly Ala Pro Phe Gly Ser Val Met Tyr Glu Phe Val Gly Lys
                245                 250                 255

Ser Ala Pro Phe Leu Ile Leu Ala Phe Leu Ala Leu Leu Asp Gly Ala
            260                 265                 270

Leu Gln Leu Cys Ile Leu Gln Pro Ser Lys Val Ser Pro Glu Ser Ala
        275                 280                 285

Lys Gly Thr Pro Leu Phe Met Leu Leu Lys Asp Pro Tyr Ile Leu Val
    290                 295                 300

Ala Ala Gly Ser Ile Cys Phe Ala Asn Met Gly Val Ala Ile Leu Glu
305                 310                 315                 320

Pro Thr Leu Pro Ile Trp Met Met Gln Thr Met Cys Ser Pro Lys Trp
                325                 330                 335

Gln Leu Gly Leu Ala Phe Leu Pro Ala Ser Val Ser Tyr Leu Ile Gly
            340                 345                 350

Thr Asn Leu Phe Gly Val Leu Ala Asn Lys Met Gly Arg Trp Leu Cys
        355                 360                 365

Ser Leu Ile Gly Met Leu Val Val Gly Thr Ser Leu Leu Cys Val Pro
    370                 375                 380

Leu Ala His Lys Asn Phe Gly Leu Ile Gly Pro Asn Ala Gly Leu Gly
385                 390                 395                 400

Leu Xaa Ile Gly Met Val Glu Ser Ser Met Met Pro Ile Met Gly His
                405                 410                 415

Leu Val Asp Pro Arg His Thr Ser Val Tyr Gly Ser Val His Ala Ile
            420                 425                 430

Ala Asp Val Ala Phe Cys Met Gly Phe Ala Ile Gly Tyr Ser Glu Ser
        435                 440                 445

Gly Leu Pro His Gly Asp Pro Val Ser Thr Gln Lys Pro Leu Pro
    450                 455                 460

Trp Thr Ser His His Gly
465                 470

<210> SEQ ID NO 3
<211> LENGTH: 30
<212> TYPE: DNA
<213> ORGANISM: Homo sapiens

<400> SEQUENCE: 3
gactaaagct taatgctccg gcccattctg                                  30

<210> SEQ ID NO 4
<211> LENGTH: 31
<212> TYPE: DNA
<213> ORGANISM: Homo sapiens

<400> SEQUENCE: 4
gaacttctag acggtcagcc atggtgactg g                                31

<210> SEQ ID NO 5
<211> LENGTH: 31
<212> TYPE: DNA
<213> ORGANISM: Homo sapiens

<400> SEQUENCE: 5
cgggatccct ccatggctcc ggcccattct g                                31

<210> SEQ ID NO 6
<211> LENGTH: 29
<212> TYPE: DNA
<213> ORGANISM: Homo sapiens

<400> SEQUENCE: 6
cgggatcccg ctcagccatg gtgactggt                                   29

<210> SEQ ID NO 7
<211> LENGTH: 34
<212> TYPE: DNA
<213> ORGANISM: Homo sapiens

<400> SEQUENCE: 7
gtccaagctt gccaccatgc tgcggcccat tctg                             34

<210> SEQ ID NO 8
<211> LENGTH: 58
<212> TYPE: DNA
<213> ORGANISM: Homo sapiens

<400> SEQUENCE: 8
ctagctcgag tcagccatgg tgactggtag cgtagtctgg gacgtcgtat gggtagca   58

<210> SEQ ID NO 9
<211> LENGTH: 465
<212> TYPE: PRT
<213> ORGANISM: Rattus sp.

<400> SEQUENCE: 9

Met Leu Gln Val Val Leu Gly Ala Pro Gln Arg Leu Lys Glu Gly
 1               5                  10                  15

Arg Gln Ser Arg Lys Leu Val Leu Val Val Phe Val Ala Leu Leu
                20                  25                  30

Leu Asp Asn Met Leu Leu Thr Val Val Val Pro Ile Val Pro Thr Phe
                35                  40                  45

Leu Tyr Ala Thr Glu Phe Lys Asp Ser Asn Ser Ser Leu His Arg Gly
        50                  55                  60

-continued

```
Pro Ser Val Ser Ser Gln Gln Ala Leu Thr Ser Pro Ala Phe Ser Thr
 65                  70                  75                  80

Ile Phe Ser Phe Phe Asp Asn Thr Thr Thr Val Glu Glu His Val
                 85                  90                  95

Pro Phe Arg Val Thr Trp Thr Asn Gly Thr Ile Pro Pro Val Thr
            100                 105                 110

Glu Ala Ser Ser Val Pro Lys Asn Asn Cys Leu Gln Gly Ile Glu Phe
            115                 120                 125

Leu Glu Glu Glu Asn Val Arg Ile Gly Ile Leu Phe Ala Ser Lys Ala
        130                 135                 140

Leu Met Gln Leu Leu Val Asn Pro Phe Val Gly Pro Leu Thr Asn Arg
145                 150                 155                 160

Ile Gly Tyr His Ile Pro Met Phe Val Gly Phe Met Ile Met Phe Leu
                165                 170                 175

Ser Thr Leu Met Phe Ala Phe Ser Gly Thr Tyr Ala Leu Leu Phe Val
            180                 185                 190

Ala Arg Thr Leu Gln Gly Ile Gly Ser Ser Phe Ser Ser Val Ala Gly
        195                 200                 205

Leu Gly Met Leu Ala Ser Val Tyr Thr Asp Asn Tyr Glu Arg Gly Arg
    210                 215                 220

Ala Met Gly Ile Ala Leu Gly Gly Leu Ala Leu Gly Leu Leu Val Gly
225                 230                 235                 240

Ala Pro Phe Gly Ser Val Met Tyr Glu Phe Val Gly Lys Ser Ser Pro
                245                 250                 255

Phe Leu Ile Leu Ala Phe Leu Ala Leu Leu Asp Gly Ala Leu Gln Leu
            260                 265                 270

Cys Ile Leu Trp Pro Ser Lys Val Ser Pro Glu Ser Ala Met Gly Thr
        275                 280                 285

Ser Leu Leu Thr Leu Leu Lys Asp Pro Tyr Ile Leu Val Ala Ala Gly
    290                 295                 300

Ser Ile Cys Leu Ala Asn Met Gly Val Ala Ile Leu Glu Pro Thr Leu
305                 310                 315                 320

Pro Ile Trp Met Met Gln Thr Met Cys Ser Pro Glu Trp Gln Leu Gly
                325                 330                 335

Leu Ala Phe Leu Pro Ala Ser Val Ala Tyr Leu Ile Gly Thr Asn Leu
            340                 345                 350

Phe Gly Val Leu Ala Asn Lys Met Gly Arg Trp Leu Cys Ser Leu Val
        355                 360                 365

Gly Met Val Ala Val Gly Ile Ser Leu Leu Cys Val Pro Leu Ala His
    370                 375                 380

Asn Ile Phe Gly Leu Ile Gly Pro Asn Ala Gly Leu Gly Phe Ala Ile
385                 390                 395                 400

Gly Met Val Asp Ser Ser Leu Met Pro Ile Met Gly Tyr Leu Val Asp
                405                 410                 415

Leu Arg His Thr Ser Val Tyr Gly Ser Val Tyr Ala Ile Ala Asp Val
            420                 425                 430

Ala Phe Cys Val Gly Phe Ala Ile Gly Pro Ser Thr Gly Gly Val Ile
        435                 440                 445

Val Gln Val Ile Gly Phe Pro Trp Leu Met Val Ile Ile Gly Thr Ile
    450                 455                 460

Asn
465
```